United States Patent [19]

Kim et al.

[11] Patent Number: 5,672,711
[45] Date of Patent: Sep. 30, 1997

[54] PROCESS FOR MANUFACTURING CEPHEM DERIVATIVES

[75] Inventors: Jung-Woo Kim, Kangseo-gu; Chong-Ryul Lee, Seocho-gu; Byung-Woo Jin, Kwanak-gu; Ki-Seok Park, Kyeonggi-do; Moo-Il Qh, Kangnam-gu, all of Rep. of Korea

[73] Assignee: Chong Kun Dang Corporation, Rep. of Korea

[21] Appl. No.: 671,726

[22] Filed: Jun. 28, 1996

[30] Foreign Application Priority Data

Jun. 30, 1995 [KR] Rep. of Korea .................. 95-18434

[51] Int. Cl.$^6$ .................. C07D 277/56; C07D 501/36; C07D 277/593

[52] U.S. Cl. .................. 548/194; 540/222

[58] Field of Search .................. 548/194

[56] References Cited

U.S. PATENT DOCUMENTS

| | | | |
|---|---|---|---|
| 4,152,432 | 5/1979 | Heymes et al. | 424/246 |
| 4,283,396 | 8/1981 | Heymes et al. | 424/246 |
| 4,376,203 | 3/1983 | Heyles et al. | 548/194 |
| 4,843,164 | 6/1989 | Heymes et al. | 548/194 |
| 4,988,816 | 1/1991 | Heymes et al. | 548/194 |
| 5,103,012 | 4/1992 | Heymes et al. | 548/194 |
| 5,336,776 | 8/1994 | Heymes et al. | 548/195 |
| 5,559,225 | 9/1996 | Negi et al. | 540/222 |
| 5,567,813 | 10/1996 | Kim et al. | 540/222 |

FOREIGN PATENT DOCUMENTS

| | | |
|---|---|---|
| 0 037 380 A2 | 7/1981 | European Pat. Off. . |
| 0 175 814 A2 | 4/1986 | European Pat. Off. . |
| 2 022 090 | 12/1979 | United Kingdom . |
| 2 025 933 | 1/1980 | United Kingdom . |
| 2 099 418 | 12/1982 | United Kingdom . |

*Primary Examiner*—John M. Ford
*Assistant Examiner*—Pavanaram K. Sripada
*Attorney, Agent, or Firm*—Nath & Associates; Gary M. Nath; Suet M. Chong

[57] ABSTRACT

The objective of this invention is to provide a process of manufacturing cephem derivatives expressed by the following formula (1), wherein the compound (2) is reacted with an condensing agent of the compound (4) and 1-hydroxy-6-trifluoromethyl benzotriazole(5) and the mixture is acylated with 7-aminocephosporanic acid (3) or its derivatives.

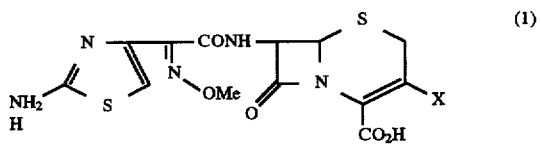

According to this invention, a desirous product with high purity may be obtained, which is more cost-saving and industrially feasible than the conventional methods, under the following process steps: Without protecting amino group of organic acid (2), conversion of the reactive derivatives under mild temperature is made and the acylation is directly carried out to obtain the final product.

11 Claims, No Drawings

PROCESS FOR MANUFACTURING CEPHEM DERIVATIVES

DETAILED DESCRIPTION OF THE INVENTION

This invention relates to a process of manufacturing cephem derivatives(1), having remarkable antimicrobial activities against Gram-positive and Gram-negative organisms.

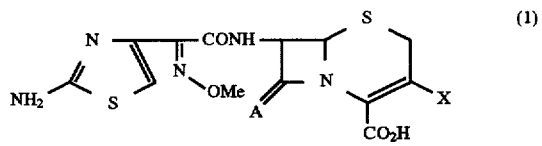

Wherein,

X represents hydrogen atom, acetoxymethyl or 1,2,4-triazin-2-methyl-6-hydroxy-3-thiomethyl-5-one.

In general, the synthesis of cephem derivatives(1) may be made available by reacting the organic acid(2) and 7-aminocephalosporanic acid (7-ACA)(3) or its derivatives.

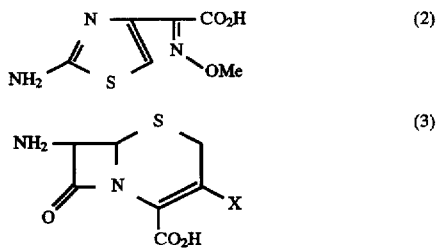

Since the direct reaction between two compounds (2) and (3) cannot be easily conducted, some researches have been made to activate the acid group of said compound (2) for acylation hereof. The methods of activating said acid group have been reported in such a manner to manufacture acid chloride, mixed acid anhydride, reactive ester or reactive amide, etc. related to said compound (2).

The process of manufacturing the acid chloride of organic acid (2) was disclosed in Japanese Patent Laid-open No. 77-102293, No. 78-34795, No. 78-68796, No. 79-52096, No. 79-157596 including U.K. Patent No. 2025933. According to these conventional methods, the acid chloride was manufactured by treating the organic acid (2) with thionylchloride (SOCl$_2$), phosphorous pentachloride (PCl$_5$), and phosphorous oxychloride (POCl$_3$). However, these methods have recognized some disadvantages in that a) their reaction conditions are very complicated, b) their industrialization is unsuitable owing to anhydrous reactions, and c) their final products are unstable with color.

Similarly, the method of activating the acid group, based on the process of manufacturing the reactive amide and mixed acid anhydride of the organic acid (2), has a disadvantage in that after protecting the amine group of organic acid (2), said protective group should be eliminated following acylation. The methods of manufacturing the reactive ester of organic acid were disclosed in the Japanese Patent Laid-open No. 79-95593, No. 77-102293 and No. 81-152488.

According to these methods, the manufacture of the compound(1) is made available by acylation with previously prepared compounds of organic acid (2), i.e., 2-pyridinethio ester, 2-benzothiazole ester and 1-hydroxybenzotriazole ester.

In an effort to said reactive ester compounds, dicyclohexylcarbodiimide (DCC) may be employed as a condensing agent, which can be also disclosed in the Korean Patent Publication No. 87-1332. In the case of manufacturing cephem derivatives on an industrial scale using said method, however, there have been the following disadvantages to be solved in the process:

a) Since dicyclohexylurea(DCU), a by-product of dicyclo carbodiimide, is produced from the condensation, the following unnecessary reaction should be required for the removal of DCU; After isolating the reactive ester of organic acid (2) generated, reaction with 7-ACA or its derivatives should be carried out.

b) Further, DCU is insoluble in water but may be partially soluble in some organic solvents including lower ahlcols, thereby its complete removal in organic solvents are not available. On top of that, now that small amounts of dicyclohexylurea (DCU) are contained as by-product in desirous cephem derivatives (1), high-purity cephem derivatives(I) may not be easily obtained.

To free from the aforementioned shortcomings, the inventor et al. have made intensive studies on acylation using various kinds of condensing agents. Using bis[4-(2,2-dimethyl-1,3-dioxolyl)methyl]carbodiimide (BDC) expressed by following formula (4) and 1-hydroxy-6-trifluoromethylbenzotriazole (FOBT) expressed by following formula (5), this invention has consequently been completed by discovering a convenient process of manufacturing the high-purity cephem derivatives (1).

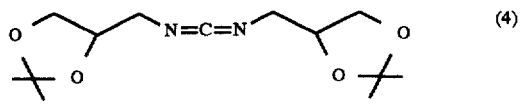

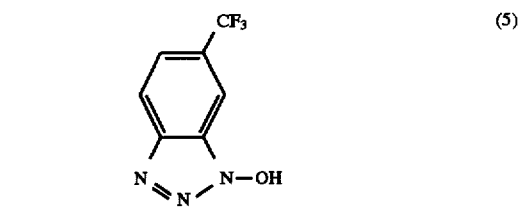

The objective of this invention is to provide a novel process of manufacturing cephem derivatives, which is better advantageous to the industrial-scale production without raising the aforementioned shortcomings.

The reaction schemes of this invention are as follows:

Scheme

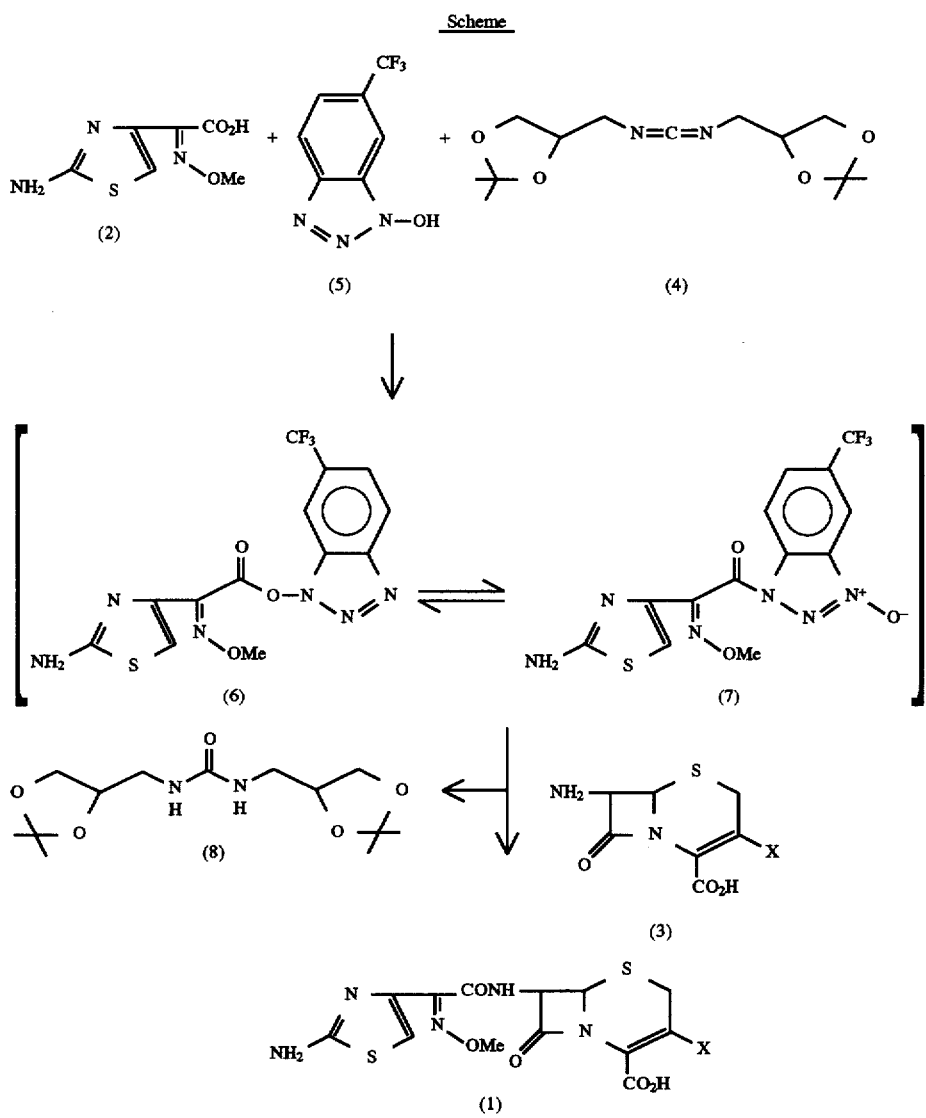

From said reactions, some appropriate solvents for manufacturing the mixture of the reactive derivatives (6) and (7) may include acetonitrile, ethylacetate, methylethylketone, acetone and tetrahydrofuran (THF); Among them, tetrahydrofuran may be most preferably used.

Each amount of FOBT and BDC in the reaction should be preferably used in 1 to 1.5 equivalent, respectively. In proportion to the weight of the compound (2), 0.1 to 10.0 wt % N,N-dimethylaniline or 4-dimethylaminopyridine is preferably used as a catalyst for this reaction. The reaction is usually conducted at 5° to 60° C. for 2 to 3 hrs in a quantitative manner.

The reaction solution without isolation and or purification is immediately added dropwise to the aqueous solution of the compound(3). Normally acylation is completed at 5° to 40° C. for 1 to 3 hrs. Hence, the appropriate base includes sodium bicarbonate, sodium carbonate and triethylamine but sodium bicarbonate is most preferably used. After completion of said acylation, the reaction mixture is extracted with ethylacetate and bis[4-(2,2-dimethyl-1,3-dioxolyl)methyl] urea(BDU) expressed by the formula (8), so formed as a by-product, is isolated as an organic layer.

Ethylacetate is added to the isolated aqueous layer and by adjusting pH at isoelectric point, FOBT(5) is dissolved to the organic layer and then, desirous derivatives(1) are obtained in precipitation. Hence, small amounts of BDU remaining at aqueous layer may be easily hydrolyzed, as illustrated in the following reaction scheme, and converted to alcohol of the formula (9), which is well soluble in water.

Thus cephem derivatives, so isolated, may be obtained in high purity.

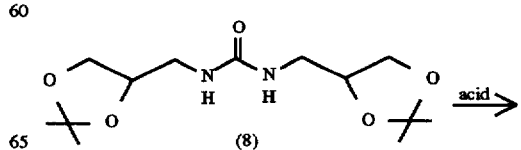

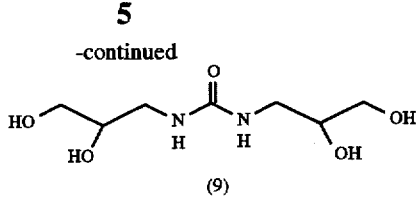

(9)

The objective of this invention is to provide a process of manufacturing cephem derivatives (I), designed to make cost-saving and industrially feasible production process in comparison to the conventional methods, under the following process steps: Without protecting its amino group, the conversion of organic acid(2) to the reactive derivatives at room temperature is available. Further, without separating it from the reacting solution, the acylation is carried out under mild temperature between the compound(3) and said reaction derivatives in a quantitative manner and then, final product(1) with high-purity may be isolated.

This invention is explained in more detail by the following examples, but the claims are not limited to these examples.

EXAMPLE 1

A mixture of FOBT (1.22 g), BDC (1.62 g) and 4-dimethylaminopyridine (0.04 g) was added to a solution of 2-(2-aminothiazol-4-yl)-2-syn-methoxyiminoacetic acid (1.01 g) suspended in THF(8 ml) and the reaction mixture was stirred at room temperature for 2.5 hrs to give a yellowish pale solution.

Meantime, 7-aminocephosporanic acid (0.95 g) was suspended in water (10 ml) and dissolved in sodium bicarbonate (1.0 g). The yellowish pale solution, previously prepared, was added dropwise to said mixture at room temperature, stirred at room temperature for 2 hrs and thus, the reaction was completed.

The reacting solution was extracted with ethylacetate to remove the organic layer containing BDU. Ethylacetate (15 ml) was added to the aqueous layer, and by adjusting pH to 2.6 using 4N HCl at 5° C., some precipitates were produced. The solution was stirred further at 0° C. for 1 hr, filtered and dried to give 1.39 g of 7-[[2-(2-aminothiazol -4-yl)-2-syn-methoxyimino]acetamido]cephalosporanic acid [cefotaxime] (yield: 87%).

IR (KBr) cm$^{-1}$ 3420, 1760, 1730, 1650, 1620, 1540, 1180

$^1$H-NMR (DMSO-d$_6$)δ 9.47 (d, 1H), 7.22 (bs, 2H), 6.70 (s, 1H), 5.60 (dd, 1H), 5.04 (d, 1H), 4.87 (d, 1H), 4.78 (d, 1H), 3.83 (s, 3H), 3.33 (q, 2H), 2.00 (s, 3H).

EXAMPLE 2

By the same procedure as described in EXAMPLE 1 except for the fact that same amounts of ethylacetate were used instead of THF, cefotaxime was obtained. Yield: 1.35 g (85%)

EXAMPLE 3

By the same procedure as described in EXAMPLE 1 except for the fact that same amounts of acetone were used instead of THF, cefotaxime was obtained. Yield: 1.37 g (86%)

EXAMPLE 4

By the same procedure as described in EXAMPLE 1 except for the fact that same amounts of methylethylketone were used instead of TFIF, cefotaxime was obtained. Yield: 1.35 g (ass)

EXAMPLE 5

By the same procedure as described in EXAMPLE 1 except for the fact that same amounts of acetonitrile were used instead of TFIF, cefotaxime was obtained. Yield: 1.34 g (84%)

EXAMPLE 6

A mixture of FOBT (1.22 g), BDC (1.62 g) and 4-dimethylaminopyridine (0.04 g) was added to a solution of 2-(2-aminothiazol-4-yl)-2-syn-methoxyiminoacetic acid (1.0 g) suspended in THF(8 ml) and the reaction mixture was stirred at room temperature for 2.5 hrs to give a yellowish pale solution.

Meantime, 7-amino-3-(2,5-dihydro-6-hydroxy-2-methyl-5-oxo-astriazin-3-yl)thiomethyl-3-cephem-4-carboxylic acid (1.3 g) was suspended in water (10 ml) and sodium bicarbonate(1.0 g) was dissolved therein. The yellowish pale solution, previously prepared, was added dropwise to said mixture at room temperature, stirred at room temperature for 3 hrs and thus, the reaction was completed.

The reacting solution was extracted with ethylacetate to remove the organic layer containing BDU. Ethylacetate (10 ml) was added to the aqueous layer and by adjusting pH to 3.0 using 4N HCl at 5° C., some precipitates were produced. The solution were stirred further at 0° C. for 1 hr, filtered and dried to give 1.74 g of 7-[[2-(2-aminothiazol-4-yl) -2-syn-methoxyamino]acetamido]-3-[(2,5-dihydro-6-hydroxy-2-m ethyl-5-oxo-as-triazin-3-yl)thiomethyl]-3-cephem-4-carboxyli ddc acid (yield: 90%).

IR (KBr) cm$^{-1}$ 1780

$^1$H-NMR(CH$_3$OH-d$_4$+DMSO-d$_6$) δ 6.83(s, 1H), 5.75(d, 1H), 5.07(d, 1H), 4.57(d, 1H), 4.27(d, 1H), 3.96 (s, 3H), 3.70 (d, 1H), 3.58 (s, 3H), 3.50 (d, 1H)

EXAMPLE 7

A mixture of FOBT (2.5 g), BDC (3.3 g) and 4-dimethylaminopyridine (0.1 g) was added to a solution of 2-(2-aminothiazol-4-yl)-2-syn-methoxyiminoacetic acid (2.0 g) suspended in THF(16 ml) and the reaction mixture was stirred at room temperature for 2.5 hrs to give a yellowish pale solution. Meantime, 7-amino-3-cephem-4-carboxylic acid (1.4 g) was suspended in water (20 ml) and sodium bicarbonate (2.0 g) was dissolved therein. The yellowish pale solution, previously prepared, was added dropwise to said mixture at room temperature, stirred at room temperature for 3 hrs and thus, the reaction was completed.

The reaction solution was extracted with ethylacetate to remove the organic layer containing BDU. Ethylacetate (15 ml) was added to the aqueous layer. Said mixture was adjusted to pH 4.5 using 4N HCl and to be cooled. After stirring for 30 mins, the insoluble materials generated were removed. The remaining solution was readjusted to pH 2.8, cooled, stirred for 3 hrs and filtered. Then, the filtrates were dried to give 2.47 g of 7-[[2-(2-aminothiazol-4-yl)-2-syn-methoxyimino]acetamido]-3-cephem-4-carboxylic acid (yield: 92%).

IR (KBr) cm$^{-1}$ 1780, 1695

$^1$H-NMR(DMSO-d$_6$)δ 9.65 (d, 1H), 7.26 (brs, 2H), 6.76 (s, 1H), 6.52(d, 1H), 5.80(dd, 1H), 5.12(d, 1H), 3.89 (s, 3H), 3.60 (bs, 2H).

What is claimed:

1. A process of manufacturing cephem derivatives of formula (1), which comprises:
   (a) reacting a compound of formula (2) with a condensing agent of formula (4) and 1-hydroxy-6-trifluoromethyl benzotriazole of formula (5) formula produce a mixture, and (b) acylating the mixture with 7-aminocephosporanic acid of formula (3) or its derivatives

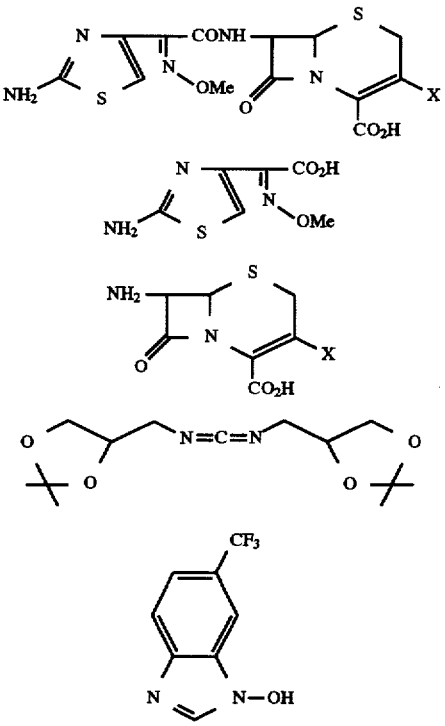

wherein,
X is hydrogen, acetoxymethyl or 1,2,4-triazin-6-hydroxy-2-methyl-3-thiomethyl-5-one.

2. A process of manufacturing cephem derivatives (1) according to claim 1, wherein said step (a) is carried out in a solvent selected from the group consisting of tetrahydrofuran, ethylacetate, acetonitrile, acetone and methylethylketone.

3. A process of manufacturing cephem derivatives (1) according to claim 2, wherein the solvent is tetrahydrofuran.

4. A process of manufacturing cephem derivatives (1) according to claim 1, wherein said step (a) is carried out in the presence of a catalyst selected from the group consisting of 4-dimethylaminopyridine or N,N-dimethylaniline.

5. A process of manufacturing cephem derivatives (1) according to claim 1, wherein said step (a) is carried out at a temperature of 5° to 60° C.

6. A process of manufacturing cephem derivatives (1) according to claim 1, wherein said step (a) is carried out without separation, and the mixture is directly acylated in said step (b).

7. A process of manufacturing cephem derivatives (1) according to claim 1, wherein said step (b) is carried out in a co-solvent consisting of water and an organic solvent.

8. A process of manufacturing cephem derivatives (1) according to claim 7, wherein said step (b) is carried out at a temperature of 5° to 40° C. for 1 to 3 hrs.

9. A process of manufacturing cephem derivatives (1) according to claim 2, wherein said step (a) is carried out in the presence of a catalyst selected from the group consisting of 4-dimethylaminopyridine or N,N-dimethylaniline.

10. A process of manufacturing cephem derivatives (1) according to claim 2, wherein said step (a) is carried out at a temperature of 5° to 60° C.

11. A process of manufacturing cephem derivatives (1) according to claim 2, wherein said step (a) is carried out without separation, and the mixture is directly acylated in said step (b).

* * * * *

UNITED STATES PATENT AND TRADEMARK OFFICE
CERTIFICATE OF CORRECTION

PATENT NO. : 5,672,711
DATED : Sep. 30, 1997
INVENTOR(S) : Jung-Woo KIM et al.

It is certified that error appears in the above-indentified patent and that said Letters Patent is hereby corrected as shown below:

Column 6, line 66, claim 1, replace "formula" with --to-- after "formula (5)".

Signed and Sealed this

Sixteenth Day of December, 1997

Attest:

BRUCE LEHMAN

Attesting Officer

Commissioner of Patents and Trademarks